US006175038B1

(12) United States Patent
Jhung et al.

(10) Patent No.: US 6,175,038 B1
(45) Date of Patent: Jan. 16, 2001

(54) METHOD OF PRODUCING AROMATIC CARBOXYLIC ACIDS BY OXIDIZING ALKYL AROMATIC COMPOUNDS OR PARTIALLY OXIDIZED INTERMEDIATES THEREOF WITH OXYGEN-ENRICHED GAS

(75) Inventors: Sung-Hwa Jhung; Youn-Seok Park, both of Taejeon-shi (KR)

(73) Assignee: Samsung General Chemicals Co., Ltd., Seosan (KR)

( * ) Notice: Under 35 U.S.C. 154(b), the term of this patent shall be extended for 0 days.

(21) Appl. No.: 09/453,535

(22) Filed: Dec. 3, 1999

(30) Foreign Application Priority Data

Dec. 22, 1998 (KR) ................................... 98-57387

(51) Int. Cl.$^7$ ..................................................... C07L 51/16
(52) U.S. Cl. ........................................... 562/412; 562/413
(58) Field of Search ..................................... 562/412, 413

(56) References Cited

U.S. PATENT DOCUMENTS

| 2,833,816 | 5/1958 | Saffer et al. . |
| 3,584,039 | 6/1971 | Meyer . |
| 5,112,992 | 5/1992 | Belmonte et al. . |
| 5,183,933 | 2/1993 | Harper et al. . |
| 5,324,702 | 6/1994 | Yoo et al. . |
| 5,359,133 | 10/1994 | Nazimok et al. . |
| 5,371,283 | 12/1994 | Kingsley et al. . |
| 5,453,538 | 9/1995 | Broeker et al. . |
| 5,523,474 | 6/1996 | Kingsley et al. . |
| 5,596,129 | 1/1997 | Murashige et al. . |
| 5,693,856 | 12/1997 | Ramachandran et al. . |
| 5,696,285 | 12/1997 | Roby . |

FOREIGN PATENT DOCUMENTS

WO 96/41791    12/1996 (WO) .

OTHER PUBLICATIONS

J. Yoo, "Selective Gas–Phase Oxidation at Oxide Nanoparticles on Microporous Materials," Catalysis Today, vol. 41 (1998), pp. 409–432.
J. Yoo, "Gas Phase Oxygen Oxidation of Alkylaromatics over CVD Fe/Mo/Borosilicate Molecular Sieve, Fe/Mo/DBH. VII. Oxidative Dehydrogenation of Alkylaromatics," Applied Catalysis A: General, vol. 142 (1996), pp. 19–29.
J. Yoo, "The CVD Fe/Mo/DBH (Deboronated Borosilicate Molecular Sieve)—Catalyzed Oxidation Reactions," Applied Catalysis A: General, vol. 143 (1996), pp. 29–51.
J. Yoo, "Gas–Phase Oxygen Oxidations of Alkylaromatics over CVD Fe/Mo/Borosilicate Molecular Sieve. VI. Effects of para–Substituents in Toluene Derivatives," Applied Catalysis A: General, vol. 135 (1996), pp. 261–271.
J. Yoo, et al., "Gas–Phase Oxygen Oxidations of Alkylaromatics over CVD Fe/Mo/Borosilicate Molecular Sieve. II. The Role of Carbon Dioxide as a Co–Oxidant," Applied Catalysis A: General, vol. 106(1993), pp. 259–273.
G. Zajac, et al., "Characterization and Oxidation Catalysis of Alkylaromatics over CVD Fe/Mo/Borosilicate Molecular Sieve: Fe/Mo/DBH," Journal of Catalysis, vol. 151, No. 2, Feb. 1995, pp. 338–348.
W. Partenheimer, "Methodology and Scope of Metal/bromide Autoxidation of Hydrocarbons," J. Chem. Soc. Chem. Commun., vol. 23 (1995), pp. 69–158.
M. Aresta, et al., "Carbon Dioxide as Modulator of the Oxidative Properties of Dioxygen in the Presence of Transition Metal Systems," J. Chem. Soc., Chem. Commun., 1992, pp. 315–317.

Primary Examiner—Paul J. Killos
(74) Attorney, Agent, or Firm—Fitzpatrick, Cella, Harper & Scinto

(57) ABSTRACT

An improved production method of aromatic carboxylic acids of significantly improved yields and quality by oxidizing alkyl aromatic substrates or their partially oxidized intermediates by oxygen-enriched gas in a conventional Co—Mn—Br catalyst system containing additional components such as a transition metal or lanthanide metal component in an aliphatic carboxylic acid having 1~6 carbon atoms. In other words, a decline in reactivity in the later part of the oxidation reaction and the precipitation of a catalyst such as manganese were effectively deterred by means of incorporating one or more than one type of transition or lanthanide metal components selected from such metals as Ce, Zr, Hf, Fe, Cr, and Mo during the oxidation reaction with oxygen-enriched gas. With this invention, pure aromatic carboxylic acids with white color can be obtained with high selectivity and reactivity by oxidation of substrates with oxygen-enriched gas. The oxidation reaction of alkylaromatic substrates proceeds more selectively with a much faster rate to produce aromatic carboxylic acids of improved quality as compared to those of conventional oxidation processes.

22 Claims, No Drawings

METHOD OF PRODUCING AROMATIC CARBOXYLIC ACIDS BY OXIDIZING ALKYL AROMATIC COMPOUNDS OR PARTIALLY OXIDIZED INTERMEDIATES THEREOF WITH OXYGEN-ENRICHED GAS

BACKGROUND OF THE INVENTION

1. Field of the Invention

The present invention discloses an improved process for oxidizing alkyl aromatic hydrocarbons and/or their partially oxidized intermediates to produce aromatic carboxylic acids. The process involves liquid-phase oxidation in the presence of a catalyst of cobalt-manganese-bromide and one or more than one transition metal or lanthanide metal component, in an aliphatic carboxylic acid having 1~6 carbon atoms such as acetic acid. In particular, one or more than one type of transition metal or lanthanide metal components are added to the conventional catalyst system of cobalt-manganese-bromide during the oxidation with oxygen-enriched gas.

The decrease in rate of the oxidation reaction of an alkyl aromatic substrate with oxygen-enriched gas in the later half of the reaction, and the precipitation of a catalyst therein were significantly deterred in the present process as compared to the conventional processes with the catalyst system of cobalt-manganese-bromide. The quality such as chromaticity of a carboxylic acid product was also significantly improved, and the side reactions to carbon dioxide were decreased in the process.

2. Description of the Related Art

As disclosed below, methods of manufacturing aromatic carboxylic acids are well known and widely used commercially. For example, a method of manufacturing of aromatic carboxylic acids such as terephthalic acid (TPA), isophthalic acid (IPA), phthalic acid, phthalic anhydride, naphthalene dicarboxylic acid, trimellitic acid, trimellitic anhydride, trimesic acid, pyromellitic dianhydride, 4,4'-biphenyldicarboxylic acid, and benzoic acid by oxidizing alkylaromatic compounds or the oxidized intermediates thereof, in the presence of cobalt-manganese-bromide, from such alkylaromatic compounds as para-xylene, para-tolualdehyde, para-toluic acid, 4-carboxybenzaldehyde (4-CBA), meta-xylene, meta-tolualdehyde, meta-toluic acid, 3-carboxybenzaldehyde, ortho-xylene, dimethylnaphthalene, pseudocumene (1,2,4-trimethylbenzene), mesitylene (1,3,5-trimethylbenzene), durene (1,2,4,5-tetramethylbenzene), pentamethylbenzene, hexamethylbenzene, 4,4'-dimethylbiphenyl and toluene is well known(for examples, U.S. Pat. Nos. 2,833,816 and 5,183,933). Such aromatic carboxylic acids are used as raw materials for manufacturing polyester after appropriate purification such as hydrogenation, etc. (U.S. Pat. No. 3,584,039). Also, polyester is widely used as a synthetic fiber, film, etc.

As an oxidant during the manufacturing of aromatic carboxylic acids, air, oxygen, or oxygen diluted with inert gas can be used. In a commercial plant, air is mainly used as an oxidant. When an oxygen-rich gas is used as an oxidant during the production of aromatic carboxylic acids, there the advantages lie in high efficiency of the gas and raw materials and the decrease in by-products and wastes. Because of these reasons, a number of cases have been known to use pure oxygen or oxygen-enriched gas as a reactant gas therein. In other words, some methods to produce TPA with pure oxygen or oxygen-enriched gas are known. For example, TPA can be produced by oxidation of para-xylene with oxygen-enriched gas and recycling of the discharged gas in the reactor into the liquid phase of the oxidation reactor (U.S. Pat. No. 5,596,129). It is also disclosed that TPA could be obtained with decreased losses of reactants and solvents by means of enhancing the efficiency of mixing and facilitating the contacts between the reactants and the reaction gas (U.S. Pat. Nos. 5,696,285, 5,523,474, and 5,371,283). It is taught that the problematic hazards in the oxidation of para-xylene such as explosion and fire can be prevented by recycling of the carbon dioxide-enriched gas produced in the oxidation (U.S. Pat. No. 5,693,856).

Nevertheless, the production methods of aromatic carboxylic acids with oxygen-enriched gas have not been applied commercially as of yet because there may be some problems such as safety problems and precipitation of metal catalysts such as manganese ($Mn^{2+}$–>$Mn^{3+}$–>$MnO_2$). The precipitation of a catalyst may cause reduction in activity, deterioration of quality such as chromaticity of the product, and decrease in efficiency of the catalyst system due to deviation from the optimum catalyst composition.

As for the catalyst system in the production of aromatic carboxylic acid, a transition metal-bromide catalyst system such as cobalt-manganese-bromide is usually used and some transition or lanthanide metal components, such as Ce, Zr, Hf, Fe, Cr, Mo, etc., can be added to improve the reactivity and quality and to decrease the side reactions. Cerium can be employed to decrease the Br concentration (U.S. Pat. No. 5,453,538). Zirconium, hafnium, nickel, iron, molybdenum, and chromium can be used to improve the efficiency of the catalyst system (U.S. Pat. Nos. 5,359,133 and 5,112,992).

Nevertheless, the case is not known in which one or more than one transition or lanthanide metal components are added to prevent a decrease in reactivity and the precipitation of a catalyst such as manganese during the oxidation of aromatic substrates by oxygen-enriched gas.

Therefore, it is very important to develop a production method of aromatic carboxylic acids with oxygen-enriched gas without the decrease in reactivity and precipitation of catalyst components.

SUMMARY OF THE INVENTION

As a result of research for resolving the above problems, the inventors herein added one or more than one type of transition metal or lanthanide metal components to the catalyst of cobalt-manganese-bromide during the manufacturing of aromatic carboxylic acids by means of oxygen-enriched gas. The inventors found that a decline in reactivity in the later part of the reaction could be prevented, in addition to an improvement of purity as in chromaticity when an appropriate amount of transition or lanthanide metal component is added to the catalyst system of cobalt-manganese-bromide. Based on such findings, the present invention has been perfected.

In view of the foregoing, in one aspect, the present invention relates to a method of producing an aromatic carboxylic acid, the method comprising the steps of oxidizing, with a gas (e.g., a feed gas) comprising oxygen, an alkyl aromatic compound or a partially oxidized intermediate thereof, using a catalyst comprising (a) cobalt, manganese, and bromine, and (b) another transition metal (i.e., other than the cobalt or manganese) and/or a lanthanide metal. Preferably, the catalyst is dissolved in a solvent comprising an aliphatic carboxylic acid having 1 to 6 carbon atoms.

In another aspect, the present invention relates to a method of producing terephthalic acid, the method comprising the steps of oxidizing para-xylene, with a gas containing oxygen, using a catalyst selected from the group consisting of (a) Co—Mn—Br—Ce, (b) Co—Mn—Br—Zr, (c) Co—Mn—Br—Mo, (d) Co—Mn—Br—Cr, and (e) Co—Mn—Br—Fe.

In yet another aspect, the present invention relates to a method of producing isophthalic acid, the method comprising the steps of oxidizing meta-xylene, with a gas containing oxygen, using a catalyst selected from the group consisting of (a) Co—Mn—Br—Ce, (b) Co—Mn—Br—Fe, and (c) Co—Mn—Br—Ce—Fe.

In a still further aspect, the present invention relates to a process of purifying crude terephthalic acid products or crude isophthalic acid products containing partially-oxidized intermediates of alkyl aromatic compounds as impurities to obtain substantially pure terephthalic acid or isophthalic acid by using an above-discussed method.

In still further aspects, the present invention relates to (a) an aromatic carboxylic acid made using an above-discussed method, (b) polyester made using the aromatic carboxylic acid, and (c) a product made using the polyester.

These and other aspects, objectives, advantages, and features of the present invention will become apparent from the following detailed description of the preferred embodiments thereof.

Unless otherwise stated, in this application, the concentration of gas is in volume %, the concentration of the catalyst is in weight ppm (by total weight of the reaction mixture), and the concentration of the product, and any other unspecified %, is in weight %.

DESCRIPTION OF THE PREFERRED EMBODIMENTS

The present invention relates to a production method of aromatic carboxylic acids, wherein alkylaromatic compounds or the oxidized intermediates thereof are oxidized by oxygen-enriched gas, with an aliphatic carboxylic acid having 1~carbon atoms as a solvent, in the presence of a catalyst of cobalt-manganese-bromide. In the process, one or more than one type of transition or lanthanide metal components are added to the conventional cobalt-manganese-bromide catalyst system.

Starting substances, i.e., alkylaromatic compounds or the oxidized intermediates thereof, to be oxidized in the present invention are preferably the compounds of benzene, naphthalene or similar aromatic compounds having one or more than one substituted alkyl groups (or a functional group having an oxidized alkyl group), such as para-xylene, para-tolualdehyde, para-toluic acid, 4-carboxybenzaldehyde, meta-xylene, meta-tolualdehyde, meta-toluic acid, 3-carboxybenzaldehyde, ortho-xylene, dimethylnaphthalene, pseudocumene (1,2,4-trimethylbenzene), mesitylene (1,3,5-trimethylbenzene), durene (1,2,4,5-tetramethylbenzene), 4,4'-dimethylbiphenyl, and toluene.

The intended substances of the present invention, i.e., aromatic carboxylic acids are preferably the compounds of benzene, naphthalene or similar aromatic compounds having one or more than one substituted carboxylic acid groups (or anhydrides with the removal of water by condensation of the carboxylic groups), such as terephthalic acid, isophthalic acid, phthalic acid, phthalic anhydrides, naphthalene dicarboxylic acid, trimellitic acid, trimellitic anhydrides, trimesic acid, pyromellitic dianhydride, 4,4'-biphenyldicarboxylic acid, and benzoic acid.

As for the basic catalyst in the present invention, a cobalt-manganese-bromide catalyst system is used. In the basic catalyst, the atomic weight ratio of manganese/cobalt is preferably 0.1~10, or more preferably 0.5~5. The atomic weight ratio of bromine/(manganese+cobalt) is preferably 0.1~10, or more preferably 0.5~2. The concentration of cobalt is preferably 20~10,000 ppm of the weight of the reactants (i.e., the substrate (the starting substance to be oxidized such as the alkylaromatic compound), the solvent, and the catalyst), or more preferably 50~1,000 ppm.

As for the source of bromide, it can be a bromine compound, such as hydrogen bromide, potassium bromide, tetrabromoethane, etc. As for the source of manganese and cobalt, compounds which are soluble in solvents, such as acetate, carbonate, acetate tetrahydrate, bromide, etc. can be used, or more preferably, as a source of cobalt, manganese, bromide, respectively, are $Co(OAc)_2 \cdot 4H_2O$, $Mn(OAc)_2 \cdot 4H_2O$, and hydrogen bromide.

The additive components used in the present invention can be any transition metal or lanthanide metal components. Specific examples include one or more than one type of selected metal components from Ce, Zr, Hf, Fe, Mo, and Cr. These additive metal components can be used in the forms of compounds having solubility in the solvents as used. Compounds such as acetate, acetate hydrate, bromide, chloride, fluoride, iodide, carbonate, carboxylate, alkoxide, azide, naphthenate, oxalate, acetylacetonate, hydroxide, nitrate, borate, and oxide can be used. Among these, an acetate or acetate hydrate compound is most preferred. The weight ratio of the additive metal component to manganese is appropriately 0.001~2, or more preferably 0.01~1. If the weight ratio is less than 0.001, the effect based on the addition of transition metal or lanthanide metal components cannot be expected. If the weight ratio is more than 2, the negative effect on the reaction such as precipitation of the added catalyst is pervasive.

The solvent used in the present invention can be any aliphatic acids of $C_1$~$C_6$, such as formic acid, acetic acid, propionic acid, n-butyric acid, isobutyric acid, pentanoic acid, hexanoic acid, trimethylacetic acid, etc., or more preferably acetic acid or the mixture of acetic acid and water. (Preferably, the solvent comprises 2–25% by weight of the solvent, of water.) The amount of solvent should be 1~10 times of the weight of an alkylaromatic compound or the oxidized intermediate compound thereof. Further, the present invention can be applied to the oxidation reaction in water as a solvent.

As for the reaction gas used in the present invention, oxygen, or a gas mixture of oxygen and an inert gas such as nitrogen can be used. The minimal pressure of the reaction is such that some portion of an alkylaromatic compound or the oxidized intermediate thereof and the solvent is maintained as liquid. The reaction pressure is appropriately 0~35 atm or more preferably 8~30 atm in terms of the gauge pressure.

The production method of aromatic carboxylic acids of the present invention can be carried out by a batch type process or a continuous process. The appropriate reaction temperature should be 100~255° C., or more preferably 175~235° C., or most preferably 180~210° C. If the reaction temperature is too low, it is impractical since the reaction rate is too slow. If the reaction temperature is too high, it is non-economical due to excessive side reactions.

According to the present invention, the quality such as chromaticity and ash content due to the precipitated Mn species of obtained aromatic carboxylic acid can be improved and the reaction rate can also be increased while maintaining the same reaction temperature. Moreover, the side reactions can be decreased and the reaction time or temperature can also be decreased while maintaining the same conversion.

The present invention is explained in detail by examples below. Nevertheless, the examples are illustrative only and should not be deemed to limit the present invention.

EXAMPLES

Examples 1 through 5 ((I) Production of terephthalic acid by the oxidation of para-xylene)

Example 1

To a titanium pressure reactor with a capacity of 450 ml, 200 g of reactants (i.e., water, para-xylene, acetic acid, and the catalyst) were added. While stirring, the reaction temperature was raised to 185° C. in the atmosphere of nitrogen. The composition of the reactants was adjusted to become 7.5% by weight of water, 15% by weight of para-xylene, and 77.5% by weight of acetic acid. Based on the total weight of reactants, the catalyst was comprised of 150 ppm of cobalt, 300 ppm of manganese, and 240 ppm of bromine. Cobalt acetate tetrahydrate, manganese acetate tetrahydrate, and hydrogen bromide were used for each catalyst component source. As for the additive transition metal or lanthanide metal components, cerium(III) acetate was added to make the concentration of cerium in the total weight of reactants to be 150 ppm. At the reaction temperature of 185° C., nitrogen was added up to 11.2 atm, and then oxygen was instantaneously added so that the pressure of the reaction became 28 atm and the concentration of oxygen in the gas phase became 60% by volume. When the reaction pressure reached 28 atm, the amount of consumed oxygen was measured with time, and the oxygen was continuously fed to maintain the same pressure of 28 atm to compensate the amount of oxygen consumed in the oxidation reaction. When the oxygen consumption reached 94.3% of the theoretical oxygen amount based on the stoichiometry of the desired oxidation reaction(reaction time: 41.0 minutes), the reactor was allowed to cool to terminate the reaction. The product obtained in this manner was subjected to a solid-liquid separation such as filtration. The solid was dried and analyzed along with the mother liquor, and the yield and purity of the product were calculated. The experimental conditions, the amount of oxygen consumed with reaction time, and the yield, purity and color of terephthalic acid product are compared with those of the Comparative Example 1 in Table 1. The yield and purity of the terephthalic acid product of this Example were similar to the run without the added transition or lanthanide metal component, the Comparative Example 1.

The results also clearly showed that the reaction rate was high, especially in the later part of the reaction, and the color property was good and the side reactions such as burning were decreased in the presence of cesium, as compared with Comparative Example 1, as shown in the run of Example 1, Table 1.

Examples 2–5

The oxidation reactions of para-xylene were carried out in the identical manner to Example 1 except that the concentration and type of the added transition or lanthanide metal component were varied to be 150 ppm of zirconium (zirconium source zirconium(II) acetate), 50 ppm of molybdenum (molybdenum source: molybdenum(II) acetate dimer), 150 ppm of chromium (chromium source: chromium (II) acetate hydrate dimer), and 150 ppm of iron (iron source: iron(II) acetate) in Examples 2, 3, 4 and 5, respectively. The experimental conditions, the amount of oxygen consumed with reaction time, and the yield, purity and color of the product are summarized in Table 1.

The yield and purity of the terephthalic acid product were similar to those in Example 1 and Comparative Example 1.

However, the rates of the oxidation reaction were high, especially in the later part of the reaction, and the color properties were good and the side reactions such as burning were decreased in the presence of each additional metal component, as compared with the Comparative Example 1, as shown in the Table 1.

Comparative Example 1

The oxidation reaction of para-xylene was carried out in the identical manner to Example 1 except that the transition or lanthanide metal component was not added in the catalyst. It required 57.5 minutes to consume the 94.3% of the theoretical amount of oxygen based on the stoichiometry of the oxidation reaction. The results are compared in Table 1. The yield and purity of the product, terephthalic acid, in the comparative Example 1 were similar to those in Example 1~5. But the reaction rate was slower in the comparative run, 57.5 minutes vs. 40.6~55.8 minutes. The side reactions such as burning were increased in the run of the Comparative Example 1 judging from the results that carbon dioxide in the spent gas was slightly increased from 17.1~20.5% by volume to 20.6% by volume. The color of the product was gray due mainly to the precipitated $MnO_2$.

Comparative Examples 2 and 3

The oxidation reactions of para-xylene were carried out in the identical manner to Example 1 except that 150 ppm of cobalt and 150 ppm of manganese were added in the catalyst as a transition or lanthanide metal component, respectively. It required 57.4 and more than 60 minutes, respectively, to consume the 94.3% of the theoretical amount of oxygen based on the stoichiometry of the oxidation reaction. The results are compared in Table 1. The yield and purity of the product, terephthalic acid, in the Comparative Example 2 was similar to those in Example 1~5 and Comparative Example 1. But the reaction rates of Comparative Examples 2 and 3 were slower, 57.4 to more than 60 minutes vs. 40.6~55.8 minutes. The side reactions such as burning were increased in the run of the Comparative Example 2 judging from the result that carbon dioxide in the spent gas was slightly increased from 17.1~20.5% by volume to 21.2% by volume. Considering the conversion of Comparative Example 3, it could also be concluded that the side reaction of Comparative Example 3 was very high. The color property was also deteriorated to dark gray and black, respectively.

TABLE 1

Results of oxidation of para-xylene (Reaction was terminated at 94.3% of the total oxygen consumption based on the stoichiometry of the desired oxidation reaction)

| Exmp. | Additive Metal Component | Concentration of Additive Metal Component (wt. ppm) | Reaction Time (Minutes)* | Consumed Oxygen with Reaction Time (mmol)** (where 10, 20, 30, and 40 are in units of minutes) | | | | TPA Yield (wt. %) | Purity of Solid TPA (wt. %) | Concentration of $CO_2$ in gas phase after Reaction (vol. %) | Color of Solid Product |
|---|---|---|---|---|---|---|---|---|---|---|---|
| | | | | 10 | 20 | 30 | 40 | | | | |
| 1 | Ce | 150 | 41.0 | 355.2 | 568.3 | 685.8 | 786.7 | 75.8 | 92.9 | 18.1 | white |
| 2 | Zr | 150 | 40.6 | 355.0 | 565.0 | 684.0 | 795.3 | 74.6 | 92.9 | 17.1 | white |
| 3 | Mo | 50 | 55.8 | 313.8 | 505.8 | 601.9 | 679.8 | 73.8 | 92.8 | 20.5 | white |
| 4 | Cr | 150 | 46.9 | 306.8 | 523.5 | 646.5 | 740.4 | 75.2 | 92.8 | 19.6 | white |
| 5 | Fe | 150 | 49.6 | 274.6 | 487.2 | 620.0 | 715.8 | 73.8 | 92.0 | 20.3 | white |
| Comp. Exmp. 1 | — | — | 57.5 | 348.1 | 546.2 | 615.3 | 681.7 | 74.2 | 92.6 | 20.6 | gray |
| Comp. Exmp. 2 | Co | 150 | 57.4 | 346.1 | 552.7 | 638.7 | 713.0 | 74.9 | 92.7 | 21.2 | dark gray |
| Comp. Exmp. 3*** | Mn | 150 | >60.0 | 353.5 | 534.7 | 593.6 | 652.3 | 65.3 | 88.6 | 19.5 | black |

*Reaction time for 94.3% of the theoretical oxygen consumption by the stoichiometry of the oxidation reaction,
**Theoretical oxygen consumption based on the stoichiometry of the oxidation reaction = 848 mmol,
***The reaction was stopped at 60 minutes of oxidation reaction and the oxygen consumption was 88.8% of the theoretical oxygen consumption by the stoichiometry of the oxidation reaction.

Examples 6 through 8 ((II) Production isophthalic acid by the oxidation of meta-xyline)

Examples 6 and 7

The oxidation reactions were carried out in the identical manner to Example 1 except that the substrate was meta-xylene and the concentration and type of the added transition or lanthanide metal component were 150 ppm of cerium (cerium source: cerium(II) acetate hydrate), and 150 ppm of iron (iron source: iron(II) acetate) in Examples 6 and 7, respectively. The experimental conditions, reaction times needed for 94.3% of the theoretical oxygen to be consumed by the stoichiometry, and colors of the product are summarized in Table 2.

It can be seen that white pure isophthalic acids are produced with the catalyst system of cobalt-manganese-bromide-cerium or cobalt-manganese-bromide-iron with high activity compared with Comparative Example 4 as shown in Table 2.

Example 8

The oxidation reaction of meta-xylene was carried out in the identical manner to Example 6 except that the concentration and type of the added transition or lanthanide metal component were both of (a) 50 ppm of cerium (cerium source: cerium(II) acetate hydrate) and (b) 50 ppm of iron (iron source: iron(II) acetate). The experimental conditions, reaction time needed for 94.3% of the theoretical oxygen to be consumed by the stoichiometry, and color of the product are summarized in Table 2.

It can be seen that white pure isophthalic acid is produced with the catalyst system of cobalt-manganese-bromide-cerium-iron with high activity compared with Comparative Example 41 as shown in Table 2.

Comparative Example 4

The oxidation reaction of meta-xylene was carried out in the identical manner to Example 6 except that transition or lanthanide metal component was not added in the catalyst system. The experimental conditions, reaction time needed for 94.3% of the theoretical oxygen to be consumed by the stoichiometry, and color of the product are summarized in Table 2.

It can be seen that impure gray isophthalic acid is produced with the catalyst system of cobalt-manganese-bromide with low activity compared with Examples 6~8.

TABLE 2

Results of oxidation of meta-xylene (Reaction was terminated at 94.3% of the total oxygen consumption based on the stoichiometry of the desired oxidation reaction)

| Example | Additive Metal Component | Concentration of Additive Metal Component (wt. ppm) | Reaction Time (Minutes)* | Color of Solid Product |
|---|---|---|---|---|
| 6 | Ce | 150 | 50.1 | White |
| 7 | Fe | 150 | 59.6 | White |

TABLE 2-continued

Results of oxidation of meta-xylene (Reaction was terminated at 94.3% of the total oxygen consumption based on the stoichiometry of the desired oxidation reaction)

| Example | Additive Metal Component | Concentration of Additive Metal Component (wt. ppm) | Reaction Time (Minutes)* | Color of Solid Product |
|---------|--------------------------|------------------------------------------------------|--------------------------|------------------------|
| 8 | Ce, Fe | 50 for each | 53.9 | White |
| Comp. Example 4 | — | — | 68.9 | Gray |

*Reaction time for 94.3% of the theoretical oxygen consumption by the stoichiometry of the oxidation reaction (Theoretical oxygen consumption based on the stoichiometry of the oxidation reaction = 848 mmol)

In summary, the present invention discloses an improved process for the production of aromatic carboxylic acids, wherein alkyl aromatic compounds or partially oxidized intermediates thereof are oxidized with a catalyst system, Co—Mn—Br with one or more than one type of transition or lanthanide metal component, in an aliphatic carboxylic acid medium, with an oxygen-enriched gas.

The oxidation reactions of alkylaromatic substrates proceed more selectively with a much faster rate to produce aromatic carboxylic acids of improved quality as compared to the conventional oxidation processes.

In other words, the precipitation of a metal catalyst such as manganese was prevented by the incorporation of one or more than one type of transition or lanthanide metal components selected from such metals as Ce, Zr, Hf, Fe, Cr, and Mo in the oxidation reaction with oxygen-enriched gas. With this invention, pure aromatic carboxylic acids with white color can be obtained by oxidation with oxygen-enriched gas with high selectivity and reactivity.

Furthermore, the oxidation reaction of the present invention can be applied to purify crude terephthalic acid products or crude isophthalic acid products containing partially oxidized intermediates of alkyl aromatic compounds as impurities to obtain substantially pure terephthalic acid or isophthalic acid, respectively. Furthermore, the aromatic carboxylic acids made by the oxidation reaction of the present invention can be used to make polyester, or other products.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A method of producing an aromatic carboxylic acid, said method comprising the steps of:
    oxidizing, with a gas comprising oxygen, an alkyl aromatic compound or a partially oxidized intermediate thereof, using a catalyst comprising (a) cobalt, manganese, and bromine, and (b) another transition metal or a lanthanide metal.

2. A method according to claim 1, wherein the catalyst is dissolved in a solvent comprising an aliphatic carboxylic acid having 1 to 6 carbon atoms.

3. A method according to claim 2, wherein the solvent contains water in an amount of 2–25% by weight of the solvent.

4. A method according to claim 1, wherein the another transition metal or the lanthanide metal is selected from the group consisting of Ce, Zr, Hf, Fe, Cr, and Mo.

5. A method according to claim 4, wherein the another transition metal or the lanthanide metal is selected from the group consisting of Ce, Fe, and Cr.

6. A method according to claim 5, wherein the another transition metal or the lanthanide metal is Ce.

7. A method according to claim 1, wherein the weight ratio of the another transition metal or the lanthanide metal to manganese is from 0.001 to 2.

8. A method according to claim 7, wherein the weight ratio of the another transition metal or the lanthanide metal to manganese is from 0.01 to 1.

9. A method according to claim 1, wherein the another transition metal or the lanthanide metal is provided by a metal compound selected from the group consisting of acetate, acetate hydrate, bromide, chloride, fluoride, iodide, carbonate, carboxylate, alkoxide, azide, naphthenate, oxalate, octanoate, acetylacetonate, hydroxide, nitrate, borate, and oxide.

10. A method according to claim 1, wherein the gas is an oxygen-enriched feed gas containing oxygen in an amount of more than 23% by volume of the stream of the gas.

11. A method according to claim 10, wherein the oxygen-enriched feed gas contains oxygen in an amount of more than 50% by volume of the stream of the gas.

12. A method according to claim 1, wherein the alkyl aromatic compound is selected from the group consisting of para-xylene, meta-xylene, ortho-xylene, pseudocumene (1,2,4-trimethylbenzene), mesitylene (1,3,5-trimethylbenzene), durene (1,2,4,5-tetramethylbenzene), pentamethylbenzene, hexamethylbenzene, dimethylnaphthalene, 4,4'-dimethylbiphenyl, and toluene.

13. A method according to claim 1, wherein the partially oxidized alkyl aromatic intermediate is selected from the group consisting of para-toluic acid, meta-toluic acid, ortho-toluic acid, para-tolualdehyde, meta-tolualdehyde, ortho-tolualdehyde, 4-carboxybenzaldehyde, 3-carboxybenzaldehyde, and 2-carboxybenzaldehyde.

14. A method according to claim 13, wherein the partially oxidized alkyl aromatic intermediate is selected from the group consisting of 4-carboxybenzaldehye, 3-carboxybenzaldehyde, para-toluic acid, and meta-toluic acid.

15. A method according to claim 1, wherein the aromatic carboxylic acid is selected from the group consisting of terephthalic acid, isophthalic acid, phthalic acid, phthalic anhydride, naphthalene dicarboxylic acid, trimellitic acid, trimellitic anhydride, trimesic acid, pyromellitic dianhydride, benzene pentacarboxylic acid, benzene hexacarboxylic acid, 4,4'-biphenyldicarboxylic acid, and benzoic acid.

16. A method according to claim 15, wherein the aromatic carboxylic acid is selected from the group consisting of terephthalic acid, phthalic acid, isophthalic acid, trimesic acid, trimellitic acid, trimellitic anhydride, and pyromellitic dianhydride.

17. A method according to claim 16, wherein the aromatic carboxylic acid is terephthalic acid.

18. A method according to claim 1, wherein both the another transition metal and the lanthanide metal are present in the catalyst.

19. A method of producing terephthalic acid, said method comprising the steps of:

oxidizing para-xylene, with a gas containing oxygen, using a catalyst selected from the group consisting of (a) Co—Mn—Br—Ce, (b) Co—Mn—Br—Zr, (c) Co—Mn—Br—Mo, (d) Co—Mn—Br—Cr, and (e) Co—Mn—Br—Fe.

20. A method of producing isophthalic acid, said method comprising the steps of:

oxidizing meta-xylene, with a gas containing oxygen, sing a catalyst selected from the group consisting of (a) Co—Mn—Br—Ce, (b) Co—Mn—Br—Fe, and (c) Co—Mn—Br—Ce—Fe.

21. A process of purifying crude terephthalic acid products or crude isophthalic acid products containing partially oxidized intermediates of alkyl aromatic compounds as impurities to obtain substantially pure terephthalic acid or isophthalic acid by using the method according to claim 13.

22. A process according to claim 21, wherein the partially-oxidized intermediates are selected from the group consisting of 4-carboxybenzaldehyde and 3-carboxybenzaldehyde.

* * * * *

UNITED STATES PATENT AND TRADEMARK OFFICE
CERTIFICATE OF CORRECTION

PATENT NO. : 6,175,038 B1
DATED : January 16, 2001
INVENTOR(S) : Sung-Hwa Jhung et al.

It is certified that error appears in the above-identified patent and that said Letters Patent is hereby corrected as shown below:

Column 3,
Line 37, "1~carbon" should read -- 1~6 carbon --.

Column 6,
Line 32, "comparative" should read -- Comparative -- and "Example" (second occurrence) should read -- Examples --.
Line 55, "Example 1~5" should read -- Examples 1~5 --.

Column 8,
Line 40, "Example 41" should read -- Example 4, --.

Column 10,
Line 57, "4-carboxybenzaldehye" should read -- 4-carboxybenzaldehyde --.

Column 12,
Line 4, "sing" should read -- using --.

Signed and Sealed this

Ninth Day of April, 2002

JAMES E. ROGAN
Director of the United States Patent and Trademark Office